United States Patent
Martin et al.

(10) Patent No.: US 6,484,144 B2
(45) Date of Patent: *Nov. 19, 2002

(54) METHOD AND SYSTEM FOR HEALTHCARE TREATMENT PLANNING AND ASSESSMENT

(75) Inventors: John Martin, State College, PA (US); Randy Nolf, Saylorsburg, PA (US)

(73) Assignee: Dental Medicine International L.L.C., Chevy Chase, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 2 days.

(21) Appl. No.: 09/396,404

(22) Filed: Sep. 15, 1999

(65) Prior Publication Data

US 2002/0004725 A1 Jan. 10, 2002

Related U.S. Application Data

(60) Provisional application No. 60/125,931, filed on Mar. 23, 1999.

(51) Int. Cl.[7] .............................................. G06F 17/00
(52) U.S. Cl. ........................................................ 705/2
(58) Field of Search ................... 705/2, 3, 4

(56) References Cited

U.S. PATENT DOCUMENTS

| 6,014,630 A | * | 1/2000 | Jeacock et al. ................ 705/3 |
| 6,029,138 A | * | 2/2000 | Khorasani et al. ............. 705/2 |
| 6,067,523 A | * | 5/2000 | Bair et al. ..................... 705/3 |

FOREIGN PATENT DOCUMENTS

| WO | WO9524010 | * | 9/1995 |
| WO | 9750046 | * | 12/1997 |
| WO | 9916407 | * | 4/1999 |

OTHER PUBLICATIONS

Derwent-Acc-No: 1998-077332;Bortolotti, M. J. et al.; Dec. 1997.*
Group Practice Managed Healthcare, V11 n7 p1 (2) Jul. 1995; Dial William F.*
James D. Beck, "Method of Assessing Risk for Periodontitis and Developing Multifactorial Models," May 1994 (Supplement), Risk Assessment and Multifactorial Models, J Periodontol vol. 65 No. 5, pp. 468–478.
Maurizio S. Tonetti, "Cigarette Smoking and Periodontal Diseases: Etiology and Management of Disease," Annals of Periodontology, Jul. 1998, vol. 3, No. 1, pp.88–101.

* cited by examiner

Primary Examiner—James P. Trammell
Assistant Examiner—Pierre E Elisca
(74) Attorney, Agent, or Firm—Fish & Richardson P.C.

(57) ABSTRACT

Methods and systems consistent with the present invention provide a comprehensive assessment and planning system. Methods and systems consistent with employ a preventive approach to predicting the likelihood of an entity entering a degraded future state by computing a risk value that reflects that likelihood. An embodiment applies to a comprehensive healthcare treatment and planning system. This healthcare system employs a preventive approach to healthcare by basing healthcare decisions on a multi-factorial computation of risk. The risk value is computed by evaluation of a function that considers a variety of historic, environmental, and systemic behaviors and conditions. In addition to considering a risk value, a treatment plan developed in accordance with the healthcare system considers symptoms and objectives of the treatment from the perspective of both the patient and the provider. The outcomes associated with treatment and risk assessment are fed back into the healthcare system to increase its accuracy and subsequent effectiveness in computing risk values over time.

48 Claims, 7 Drawing Sheets

METHOD AND SYSTEM FOR HEALTHCARE TREATMENT PLANNING AND ASSESSMENT

RELATED APPLICATIONS

The following identified U.S. patent application is relied upon and is incorporated by reference in this application: Provisional U.S. Patent Application No. 60/125,931, entitled "Method and System for Healthcare Treatment Planning and Assessment," filed on Mar. 23, 1999.

FIELD OF THE INVENTION

The present invention relates generally to data processing systems and, more specifically, to an assessment and planning system that uses a multi-factorial computation of risk to determine an appropriate strategy for preventing an entity from entering an undesirable state.

BACKGROUND OF THE INVENTION

A patient generally seeks medical advice and treatment from a healthcare provider when the patient experiences a medical condition that the patient is unable to treat. The term healthcare as used herein refers generally to any activity directed to the care and maintenance of a patient (e.g., a human being). A healthcare provider may thus provide services directed to the mental, emotional, or physical well-being of a patient. Accordingly, healthcare providers may include, for example, psychiatrists, podiatrists, dentists, substance abuse counselors, etc. A healthcare provider diagnoses a condition, or disease, and recommends a course of treatment to cure the condition, if such treatment exists. This model of reparative healthcare treatment focuses only on healing, or repairing, an existing condition.

To determine an appropriate treatment for an existing condition, a healthcare provider runs a series of diagnostic tests and collects clinical data related to the patient's symptoms. The term "clinical data" refers to the data measured and observed by a healthcare provider during examination of a patient, reflecting the patient's health, or related to a health condition. The clinical data generally reflects the effects of a disease as determined at a point in time. For example, if a patient has a tumor, a healthcare provider may collect clinical data reflecting the tumor's size, appearance, location, and texture.

After collecting the clinical data, the healthcare provider forms hypotheses about the cause of the condition, its severity, and its impact. Next, the healthcare provider diagnoses the condition and determines how to treat the condition. The patient only provides input into this process by enumerating symptoms and giving background information about the condition or related conditions.

Alternatively, a patient or healthcare provider may input clinical data into a computer program that calculates a value of risk. The risk value output by the computer program is a quantified measure indicating a patient's likelihood of currently having a condition or disease as indicated by the patent's symptoms. This computed value of risk may be considered in diagnosing a condition or disease.

For example, consider a situation where a patient enters a dentist's office with red, swollen gums, extreme sensitivity to both hot and cold substances, and pain in several areas of her mouth. The dentist hypothesizes that the patient has periodontal disease. Or alternatively, the dentist inputs an enumerated list of the patient's symptoms into a computer program which outputs a quantified indicator of the patient's likelihood of either having periodontal disease, or if the patient's periodontal disease is in remission, having an exacerbation of the periodontal disease.

Before proceeding with a diagnosis and plan for treatment, suppose the dentist runs a series of tests and makes observations to determine the accuracy of the initial hypothesis or indicator value. During the examination, suppose the dentist finds significant bone loss associated with several teeth and decides to restore the areas of bone loss with a bone graft procedure. After performing the bone graft procedure, the dentist submits claim forms to the patient's insurance carrier for approval. The dentist may further recommend that the patient initiate a scheme of improved oral hygiene, including regular professional cleaning appointments to minimize or retard the effects of periodontal disease. Absent any obviously related complications, the patient and dentist consider the treatment a success and continue their relationship. If the insurance company refuses payment the patient must absorb the cost of the procedure.

This reparative model for healthcare treatment fails to consider how a patient's intended behavior impacts the effectiveness of the treatment. In the example above, the patient's condition may have been exacerbated by the patient's smoking habit that the patient has no intention of ceasing. Additionally, the patient may be unable or unwilling to improve her oral hygiene. Both of these factors contribute to the effectiveness and longevity of a bone graft procedure. The model also fails to direct treatment towards the prevention of future conditions. For instance, in the example above, the patient's periodontal disease is likely to worsen over time, absent any changes in the patient's oral care. The bone graft procedure used to treat the most severe areas of bone loss fails to retard, prevent, or otherwise impact other areas of the patient's gums that have been effected by the periodontal disease. Therefore, performing a bone graft, an intrusive and unpredictable procedure, as the only form of treatment, may not be the best treatment because it fails to address the likely progression of the disease and a potential need for subsequent treatment related to a current condition. A reparative treatment planning scheme fails to consider that current symptoms reflect only one indicator of the significance or severity of a condition. Further, the reparative model for treatment fails to consider the patient's medical history and its impact on the effectiveness and longevity of treatment.

Overall, the reparative model for healthcare treatment planning focuses solely on healing an existing condition as indicated by diagnostic tests and clinical data. This model fails to consider various other factors that impact the effectiveness of treatment. As a result, the most effective and comprehensive treatment may not be administered. Similarly, because the reparative model fails to focus on preventing future conditions, it is likely to result in a higher number of procedures needed on a long-term basis. Patients and insurance companies experience inflated economic healthcare costs when healthcare providers administer unnecessary, overly intrusive, or ineffective treatment, or treatment that contributes to a new disease. Additionally, patients absorb high non-economic costs, in the form of emotional, mental, or physical anxiety, when they are subjected to unnecessary or overly intrusive procedures, as determined in light of the patient's overall state of health. It is therefore desirable to improve healthcare systems.

BRIEF DESCRIPTION OF THE DRAWINGS

The accompanying drawings, which are incorporated in and constitute a part of this specification, illustrate an implementation of the present invention and together with the description, serve to explain the advantages and principles of the invention. In the drawings.

SUMMARY OF THE INVENTION

Figure 1:
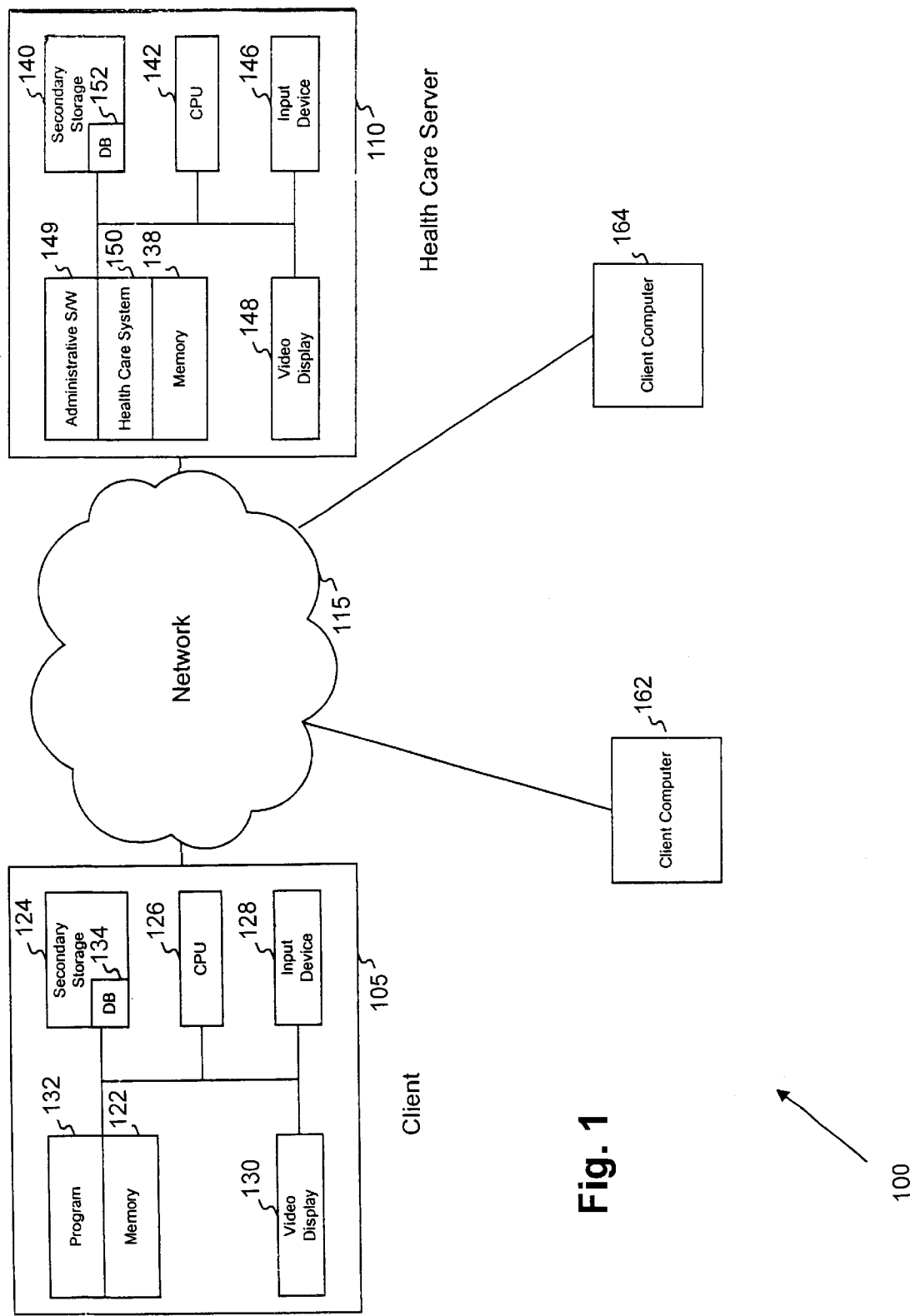
FIG. 1 depicts an exemplary data processing system suitable for use with methods and systems consistent with the present invention.

In accordance with a first aspect of the present invention, as embodied and broadly described herein, a method is implemented in a data processing system for computing a risk value that indicates a likelihood of an entity entering an undesirable state. The system receives data reflecting a current state of an entity and computes a risk value that reflects a likelihood of the entity entering the undesirable state, based on a subset of the received data. The system then analyzes a proposed strategy for preventing the entity from entering the undesirable state.

Furthermore, in accordance with a first aspect of the present invention, a method is implemented where the entity is a patient.

Consistent with an embodiment of the first aspect of the present invention, as embodied and broadly described herein, a method is implemented in a data processing system for determining an appropriate treatment for a patient. The system receives data reflecting a current state of the patient and computes a risk value that reflects a likelihood of the patient developing a disease, based on a subset of the diagnostic data. The system then analyzes a proposed treatment plan, considering the computed risk value and the received diagnostic data.

Furthermore, in accordance with an embodiment of the method of the first aspect of the present invention, as embodied and broadly described herein, a method is implemented in a data processing system for determining an appropriate treatment for a patient. The system receives data reflecting a current state of the patient and computes a risk value that reflects a likelihood of the patient being responsive to treatment, based on a subset of the diagnostic data. The system then analyzes a proposed treatment plan, considering the computed risk value and the received diagnostic data.

Furthermore, in accordance with an embodiment of the method of the first aspect of the present invention a method is performed for a plurality of patients to identify an adjustment to the risk value that will render the risk value more accurate and adjust the risk value accordingly.

Furthermore, in accordance with an embodiment of the method of the first aspect of the present invention the diagnostic data includes clinical data, objectives of treatment, and data reflecting factors that may positively or negatively impact the success of treatment. In accordance with this aspect of the present invention, the computation of the risk value includes analyzing the diagnostic information.

Furthermore, in accordance with an embodiment of the method of the first aspect of the present invention a treatment plan is assessed for its suitability in treating a condition based on the computed risk value and the diagnostic data.

In accordance with an embodiment of the first aspect of the present invention, as embodied and broadly described herein, an apparatus is provided that includes a client and a healthcare server. The system further includes a storage device including patient health information, a memory including administrative software and a healthcare system, and at least one processor for executing the healthcare system and the administrative software.

DETAILED DESCRIPTION

Methods and systems consistent with the present invention generally provide a comprehensive assessment and planning system that employs a preventive approach to predicting the likelihood of an entity entering an undesirable future state. Additionally, based on a value of an indicator that reflects the likelihood of an entity entering an undesirable state, methods and systems consistent with the present invention assess the appropriateness of a strategy proposed to avoid, or limit, the entity from entering the undesirable state. One embodiment of a method and system consistent with the present invention is described below relative to healthcare.

A healthcare treatment and planning system (hereinafter "healthcare system") consistent with the present invention enables assessment of a patient's current and likely future health and the effectiveness of healthcare decisions. Unlike current methods and systems which only assess a patient's likelihood of currently having a condition or disease, methods and systems consistent with the present invention employ a predictive approach to healthcare treatment decision-making. The healthcare system thus provides healthcare according to a preventive model, where a multifactorial computed risk value is used to prescribe an appropriate treatment for an existing condition, and to prevent a condition from occurring. Accordingly, methods and systems consistent with the present invention formulate a health treatment plan by considering input from various factors that impact a patient's likelihood of developing disease and the likelihood that a particular course of treatment will be effective for the patient. This comprehensive, preventive treatment planning model requires fewer procedures on a long-term basis, thereby yielding higher quality, more effective, and lower cost healthcare. The risk value reflects an integrated computation of environmental factors, current health conditions, intended patient behavior, and effectiveness of prior treatment both for a particular patient and for a large group of unrelated patients. The predictive model of healthcare employed by methods and systems consistent with the present invention supports early diagnosis, interceptive treatment, and behavior modification.

Overview

Treatment planning directed to maintaining health and preventing future conditions reduces the long-term costs associated with healthcare. To achieve a preventive model of healthcare, treatment planning considers factors beyond current symptoms that impact a condition. Thus, such a model expands the focus of healthcare to consider those factors that directly or indirectly lead to future disease occurrences. Various behavioral elements contribute to a patient's likelihood of developing a disease and the likely success of treatment. The objective of comprehensive and preventive treatment planning is to determine which treatment will achieve with acceptable predictability the most desirable set of outcomes based on a patient's desires, conditions, risk factors, susceptibility, and healing capacity. Such a plan decreases healthcare costs for patients and insurance companies by increasing the effectiveness of treatment and treatment planning decisions of healthcare providers. The impact of a patient's desires, conditions, susceptibility, and healing capacity on the patient's health may be expressed as a probability in terms of a risk of the patient developing disease or responding to treatment.

Generically speaking, risk is a measure of a loss, expressed as a probability. A loss occurs as the result of some course of events that may include interrelated factors and events, possibly occurring over a long period of time. An event may be perceived as a loss in one context, but not in another. For example, in healthcare the extraction of a tooth is a loss for a patient, but may be a gain for an insurance company because the extraction allows the insurance company to avoid future losses associated with the extracted tooth.

Managing risk requires identification of the conditions, events, and behaviors that contribute to a loss and a course of action to mitigate their effects. An effective risk management strategy thus focuses on identifying and controlling the conditions, events, or behaviors that contribute to or prevent the occurrence of a loss. Once the relevant conditions, events and behaviors have been identified, the effective courses of action to reduce risk may be determined and analyzed with respect to cost and outcome.

As applied to healthcare, a loss may be identified as a health condition. By considering factors impacting a patient's health, that patient's risk of experiencing certain health conditions may be determined. Relevant factors to consider in determining an appropriate risk value may include systemic, psychological and environmental conditions, events, and behaviors, including, for example, age, climate, and marital status. Once a healthcare provider determines an accurate measure of a multi-factorial risk value, the provider may develop a treatment plan directed to curing current conditions and preventing future ones, while maintaining a specified level of health. Such a preventive model of healthcare yields lower costs for patients and insurance companies and increases the effectiveness and predictability of healthcare overall.

Methods and systems operating in accordance with the present invention implement a risk-based approach to healthcare treatment and treatment planning by providing a healthcare provider with a risk assessment tool located at the provider's site. During an examination of a patient, the healthcare provider inputs a variety of clinical data and data reflecting the patient's behavior into a risk assessment tool. The tool computes a value of risk that reflects relationships between the inputs, and is effective for predicting an appropriate treatment plan. A healthcare provider develops a treatment plan, taking into account the patient's symptoms and the computed risk value. The healthcare system analyzes the plan and evaluates its appropriateness.

Once a treatment plan has been implemented, the healthcare system analyzes the outcomes of treatment as a measure of the effectiveness of the plan. An effectiveness rating reflects a measure of the actual outcome of treatment against the expected outcome of the treatment. A value representing the effectiveness of a particular course of treatment is fed back into the risk assessment tool, thereby impacting future computations of risk to allow the system to increase its accuracy in determining risk over time.

Implementation Details

FIG. 1 depicts a data processing system 100 suitable for practicing methods and systems consistent with the present invention. Data processing system 100 includes client computer 105 connected to server computer 110 via network 115. Client computer 105 includes a memory 122, a secondary storage device 124, a central processing unit (CPU) 126, an input device 128, and a video display 130. A program 132, performing organization management and administrative functions, operates in memory 122. The program is suited to the particular client computer. For example, if the client computer is situated in a healthcare provider's office, the program may be directed to managing the healthcare provider's practice, including scheduling and tracking patients. In the secondary storage device 124 resides a database 134 containing a subset of a database maintained at the server computer and including the subset of data needed by a particular client computer 105. For example, if the client computer 105 is situated in a healthcare provider's office, database 134 may contain patient records.

A healthcare server computer 110 includes a memory 138, a secondary storage device 140, a CPU 142, an input device 146, and a video display 148. Memory 138 includes administrative software 149 and a healthcare system 150. Administrative software 149 includes, for example, a module that coordinates access to the healthcare server computer 110 by various client computers 105. A healthcare system 150 implements a preventive scheme of treatment planning where treatment reflects a computed value of risk, updated regularly by the system to ensure accuracy. Secondary storage device 140 includes a database 152 that may be accessed by any of the client computers having appropriate authorization. The ability of a system consistent with the present invention to distribute database information among various computers in various locations further supports maintenance of a central repository of patient health data, reflecting data collected by various healthcare providers during the patient's life, accessible to authorized entities.

The client computers 162 and 164 are similarly configured to client computer 105. These computers may be located at an insurance company or a research organization, and may perform a variety of data analysis functions. For example, if located at an insurance company, a client computer may gather and analyze data collected by the healthcare system for the purpose of determining economically viable treatment alternatives for various conditions and levels of risk. Similarly, a client computer at an insurance company may assess outcomes information collected by the healthcare system to compare methods and results of treatment planning among providers to determine which providers to approve. A client computer at a research organization may perform a similar function of comparing data collected by the healthcare system to determine treatment planning trends and provide suggestions regarding effective treatment plans for specified conditions and levels of risk.

One skilled in the art will appreciate that client computer 105 and healthcare server computer 110, although depicted with various components, may contain additional or different components. Additionally, network 115 may include a wide area network, like the Internet, or a local area network. Furthermore, although aspects of the present invention are described as being stored in memory, one skilled in the art will appreciate that these aspects can also be stored on or read from other types of computer-readable media, such as secondary storage devices, like hard disks, floppy disks, a CD-ROM, or other forms of RAM or ROM. Still further, one skilled in the art will appreciate that databases 134 and 152 and administrative software 149 may be stored on or distributed across other devices on the network 115.

Figure 2:
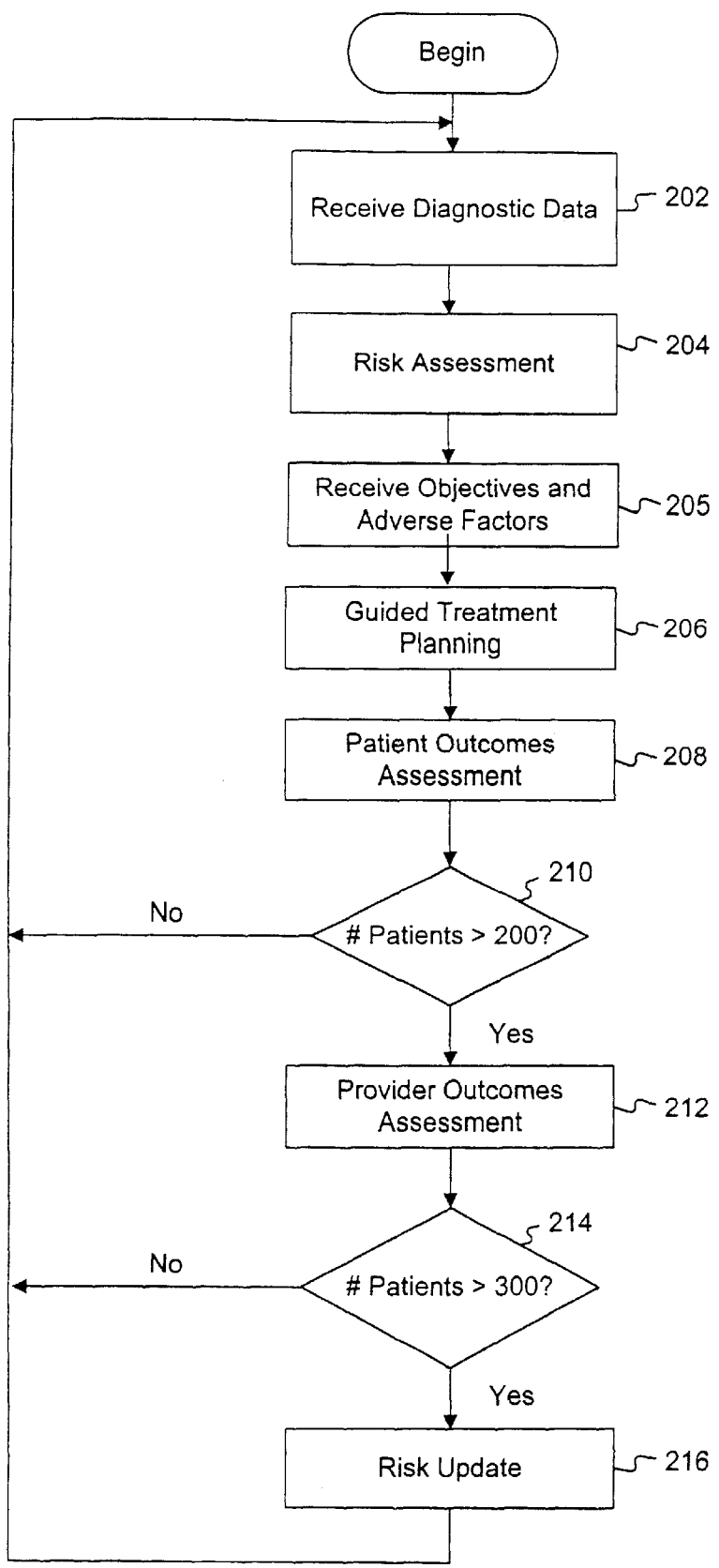
FIG. 2 depicts a flowchart of the steps performed by the healthcare system depicted in FIG. 1.

FIG. 2 depicts a flowchart of the steps performed by the healthcare system. An exemplary embodiment is described below relative to a dentist although one skilled in the art will appreciate that the present invention can be used in other health-related or non-health-related fields. Each of the steps of FIG. 2 will be discussed in greater detail relative to the discussion of FIGS. 3–7.

First, the healthcare system receives diagnostic information collected by a healthcare provider during an examination (step 202). This information is provided by a healthcare provider. The term "diagnostic information" refers to (1) clinical data observed and measured by a healthcare provider, and (2) personal health history information. The diagnostic information captures data reflecting a patient's overall health situation, including physical, current and historical environmental conditions, events, and behaviors.

The clinical data reflects clinical conditions or behaviors, either existing, or found to have an increased risk of occurring, that justify treatment beyond routine maintenance as determined by a healthcare provider during an examination of a patient. A healthcare provider determines clinical conditions by taking measurements and making observations. For example, swelling, appearance, and thermal sensitivity of a surface growth may be observed and measured by a provider during an examination. Table 1 lists an exemplary set of clinical data considered by the healthcare system. The system initializes the value of each clinical condition to 0 indicating that the clinical condition does not exist.

If a patient has a specified clinical condition, the healthcare system quantifies the condition by assigning it an appropriate value according to the values listed in Table 1. The "site" column in Table 1 receives input identifying a location, i.e., a tooth or segment of the mouth, in which the condition exists. The six segments considered by the healthcare system are discussed below relative to step 318 of FIG. 3.

TABLE 1

| Clinical Conditions | Yes | No | Site |
|---|---|---|---|
| 1. Pain, discomfort, thermal sensitivity | 1 | 0 | |
| 2. Swelling, infection | 1 | 0 | |
| 3. Unacceptable appearance | 1 | 0 | |
| 4. Caries | 1 | 0 | |
| 5. Pulpitis or necrosis | 1 | 0 | |
| 6. Fractures of clinical crown | 1 | 0 | |
| 7. Limited embrasure space | 1 | 0 | |
| 8. Inadequate remaining tooth structure | 1 | 0 | |
| 9. Missing teeth | 1 | 0 | |
| 10. Restoration with inadequate retention or physiologic design | 1 | 0 | |
| 11. Retained deciduous teeth | 1 | 0 | |
| 12. Prostheses with inadequate retention or physiologic design | 1 | 0 | |
| 13. Attrition | 1 | 0 | |
| 14. Erosion | 1 | 0 | |
| 15. Inadequate access to sound tooth structure | 1 | 0 | |
| 16. Root fractures | 1 | 0 | |
| 17. Root proximity | 1 | 0 | |
| 18. Mobility | 1 | 0 | |
| 19. Periodontal inflammation | 1 | 0 | |

TABLE 1-continued

| Clinical Conditions | Yes | No | Site |
|---|---|---|---|
| 20. Pathologic sulcus deeper than 5 mm, pocket depth | 1 | 0 | |
| 21. Radiographic evidence of disease, bone loss | 1 | 0 | |
| 22. Inadequate attached gingiva | 1 | 0 | |
| 23. Aberrant frena | 1 | 0 | |
| 24. Oral lesion, non-periodontal | 1 | 0 | |
| 25. Inadequate oral hygiene | 1 | 0 | NA |
| 26. Non-physiologic bone/gingiva architecture | 1 | 0 | |
| 27. Malocclusion - inter-arch tooth alignment | 1 | 0 | |
| 28. Malocclusion due to restoration or prosthesis | 1 | 0 | |
| 29. Tooth position - intra-arch | 1 | 0 | |
| 30. TMJ dysfunction | 1 | 0 | NA |
| 31. Athletic participation | 1 | 0 | NA |
| 32. Impacted teeth | 1 | 0 | |
| 33. Skeletal or mucosal abnormalities | 1 | 0 | |
| 34. Abnormal growth (soft or hard tissue) | 1 | 0 | |
| 35. Oral habit | 1 | 0 | NA |
| 36. Tobacco use | 1 | 0 | NA |
| 37. Diet or eating disorder | 1 | 0 | NA |
| 38. Bleeding | 1 | 0 | NA |
| 39. Numbness or paresthesia | 1 | 0 | NA |
| 40. Inadequate bone volume | 1 | 0 | |
| 41. Furcation | 1 | 0 | |

The term personal health history refers to a standard set of personal health information collected by a healthcare provider. For example, information reflecting a patient's current and/or past medications, laboratory test results, behaviors, environmental exposures, and family health history may be gathered by a healthcare provider during an examination of a patient. Table 2, below, lists an exemplary set of personal health history data and their corresponding values used by the healthcare system.

TABLE 2

| Personal Health History | Value |
|---|---|
| 1. Parental history of periodontitis | |
| None | 0.8 |
| Had periodontitis | 1.3 |
| Had tooth loss due to periodontitis | 1.4 |
| Unknown | 1 |
| 2. Patient's history of diabetes | |
| Do not have | 1 |
| Controlled diabetic | 1 |
| Uncontrolled diabetic | 1.1 |
| Unknown | 1 |
| 3. Patient's use of cigarettes | |
| Don't use cigarettes | 1 |
| Smoke less than 10 per day | 1.2 |
| Smoke more than 10 per day | 1.3 |
| Unknown | 1 |
| 4. Number of Annual Professional Cleanings | |
| 1 (or less) per year | 0 |
| 2 per year | −4 |
| 3 (or more) per year | −10 |

After receiving the diagnostic information, the healthcare system computes a risk value that reflects a likelihood that a condition will occur (step 204). In this step, the system quantifies a subset of the diagnostic information collected relative to step 202. The subset of the diagnostic information quantified to compute a value of risk includes the set of data indicated by scientific data analysis and study as having an impact on a patient's likelihood of developing disease and being responsive to treatment. Because the data used to compute a risk value is a subset of diagnostic information regularly collected by a healthcare provider, the set of data considered in computing the risk value may be changed without altering the design of the healthcare system, i.e. introducing additional variables or risk factors. The computation of a risk value also considers data generated during a risk adjustment process, described below with respect to step 216. This computed risk value contributes to the decision process of treatment planning. "Treatment restrictions" is a term used to refer to limitations of treatment that may be imposed, as necessitated by the computed value of risk. For example, an aggressive, highly unpredictable procedure may not be appropriate for a high risk patient. Accordingly, the aggressive, highly unpredictable procedure serves as a treatment restriction for that patient. Treatment restrictions may be considered by a healthcare provider, a healthcare payor (e.g., an insurance company), or a healthcare policy maker in determining the appropriate limitations of treatment. A healthcare payor or policy maker may further consider these restrictions when determining which benefits are allowable under particular benefit plans.

The healthcare system then receives information reflecting patient and provider objectives of care, and information reflecting events, behaviors, or conditions that may adversely impact the success of a treatment plan (step 205).

Patient and provider objectives include data reflecting the patient's and provider's objectives regarding treatment. Patient objectives reflect certain of a patient's present and intended behaviors and the patient's objectives in obtaining treatment. Provider objectives reflect certain of a provider's objectives in assigning a course of treatment. By considering the patient and provider objectives of a treatment plan, the treatment plan may be tailored to meet those objectives, thereby increasing its subjective utility. Table 3 categorizes and lists an exemplary set of patient and provider objectives, and the values assigned to each by the healthcare system. The healthcare system initializes the value of each objective to 0.

TABLE 3

Objectives of Treatment

| | Yes | No |
|---|---|---|
| Patient Objectives | | |
| 1. Improve current function (chewing, eating) | 1 | 0 |
| 2. Improve current comfort | 1 | 0 |
| 3. Improve current appearance | 1 | 0 |
| 4. Repair broken or diseased structures | 1 | 0 |
| 5. Prevention/Reduce risk of disease | 1 | 0 |
| 6 Spread treatment over several years to reduce annual cost | 1 | 0 |
| 7. Out-of-pocket cost | 1 | 0 |
| 8. Total cost | 1 | 0 |
| 9. Minimize cost for future treatment | 1 | 0 |
| 10. Date treatment must be completed by | 1 | 0 |
| 11. Appointments - number or time | 1 | 0 |
| 12. Alleviate current pain | 1 | 0 |
| 13. Control treatment pain and anxiety | 1 | 0 |
| 14. Prevent tooth loss | 1 | 0 |
| Behavior Modification | | |
| 15. Improve oral hygiene | 1 | 0 |
| 16. Decrease or eliminate tobacco use | 1 | 0 |
| 17. Improve diet | 1 | 0 |
| 18. Improve exercise | 1 | 0 |
| 19. Comply with prescribed drug regimen | 1 | 0 |
| 20. Comply with agreed upon treatment recommendations | 1 | 0 |
| Provider Objectives - Clinical Characteristics - General | | |
| 21. Improve appearance | 1 | 0 |
| 22. Create a physiologic occlusion | 1 | 0 |
| 23. Resolve the non-periodontal inflammatory lesion | 1 | 0 |
| 24. Satisfy the patient's objectives | 1 | 0 |
| 25. Improve function | 1 | 0 |
| 26. Maintain health, appearance and function | 1 | 0 |
| Provider Objectives - Clinical Characteristics - Periodontal | | |
| 27. Eliminate clinical signs of inflammation | 1 | 0 |
| 28. Reduce probing depths to less than 5 mm | 1 | 0 |
| 29. Improve accessibility for maintenance | 1 | 0 |
| 30. Decrease mobility | 1 | 0 |
| 31. Enhance the zone of attached gingiva | 1 | 0 |
| 32. Create adequate clinical crown length | 1 | 0 |
| 33. Slow the inflammatory lesion's progression | 1 | 0 |
| Provider Objectives - Clinical Characteristics - Restorative | | |
| 34. Control caries progression | 1 | 0 |
| 35. Create restorations that have marginal integrity | 1 | 0 |
| 36. Create restorations that have physiologic form | 1 | 0 |
| 37. Create restorations that have proper contacts | 1 | 0 |
| 38. Restore vertical dimension of occlusion | 1 | 0 |

The healthcare system also receives diagnostic information that corresponds to tentative factors that may adversely affect treatment predictability. By considering these factors during the treatment planning process, a treatment plan will account for these factors and is therefore more likely to achieve its expected result. Table 4, below lists an exemplary set of tentative factors considered by the healthcare system. The healthcare system initializes the value of each adverse factor to 0.

TABLE 4

| Adverse Factors | Yes | No | Site |
|---|---|---|---|
| 1. Tobacco use | 1 | 0 | NA |
| 2. Poor oral hygiene | 1 | 0 | NA |
| 3. Oral habits | 1 | 0 | NA |
| 4. Occlusal stress, bruxism | 1 | 0 | NA |
| 5. Diet or eating disorder | 1 | 0 | NA |
| 6. Systemic disease or its treatment | 1 | 0 | NA |
| 7. Xerostomia | 1 | 0 | NA |
| 8. Radiation therapy | 1 | 0 | NA |
| 9. Hormonal changes | 1 | 0 | NA |
| 10. Susceptibility to periodontal disease | 1 | 0 | NA |
| 11. Susceptibility to caries | 1 | 0 | NA |
| 12. Presence of pathogenic bacteria | 1 | 0 | NA |
| 13. Friable or poor tissue quality | 1 | 0 | NA |
| 14. Thin periodontium | 1 | 0 | |
| 15. Poor healing capacity | 1 | 0 | NA |
| 16. Mental illness or impairment | 1 | 0 | NA |
| 17. Physical impairment | 1 | 0 | NA |
| 18. Access problems | 1 | 0 | |
| 19. Anatomical limitations | 1 | 0 | |
| 20. Tooth position | 1 | 0 | |
| 21. Limited embrasure space | 1 | 0 | |
| 22. Root proximity | 1 | 0 | |
| 23. Inadequate remaining tooth structure | 1 | 0 | |
| 24. Canal morphology | 1 | 0 | |
| 25. Calcified canals | 1 | 0 | |
| 26. Bone architecture | 1 | 0 | |
| 27. Excessive edentulous span length | 1 | 0 | |
| 28. Crown to root ratio | 1 | 0 | |
| 29. Root morphology | 1 | 0 | |
| 30. Structural strength of the tooth | 1 | 0 | |
| 31. Bone volume | 1 | 0 | |
| 32. Bone quality | 1 | 0 | |
| 33. Tooth mobility | 1 | 0 | |
| 34. Inadequate anchorage | 1 | 0 | NA |
| 35. Inter-occlusal space | 1 | 0 | |
| 36. Occlusion | 1 | 0 | NA |

The healthcare system then receives a proposed treatment plan, input into the system by a healthcare provider, determines whether the plan is appropriate, and predicts its effectiveness (step 206). The proposed treatment plan includes treatment for healing existing conditions and preventing the occurrence of future conditions. In proposing a plan, a healthcare provider considers the computed risk value, the diagnostic information, treatment restrictions, the patient and provider objectives, and any factors that may adversely affect treatment. The plan is input into the healthcare system as a series of treatment codes that correspond to types of treatment.

After receiving a proposed treatment plan, the healthcare system analyzes the series of treatment codes to determine whether the plan is appropriate. During analysis of a plan, the healthcare system compares the proposed plan with a set of treatment codes representing an appropriate treatment plan as determined by the healthcare system. Although the healthcare system does not provide a proposed plan, it evaluates each of the relevant treatment codes relative to the diagnostic data received and risk value computed to determine if a particular treatment is appropriate. The healthcare system determines the appropriateness of a plan by analyzing data contained in its series of tables.

For example, the healthcare system includes a database that maintains a list of objectives matched with clinical conditions, and a database of clinical conditions matched with appropriate treatment. During analysis of the plan, the healthcare system determines whether each objective corresponds to a clinical condition and whether each clinical condition corresponds to an appropriate treatment, and vice versa. The healthcare system also includes a database that maintains a list of treatment codes, matched with conditions, or factors, that may reduce the predictability of treatment. The healthcare system includes a predetermination section that notifies a healthcare provider and an insurance company if a proposed plan fails to appropriately address objectives, clinical conditions, and treatment. Therefore, for example, if a proposed plan includes a treatment that is matched with a condition that has been flagged as potentially reducing the predictability of treatment, the healthcare system may alert a user accordingly.

After reviewing the healthcare system's analysis of a plan, a healthcare provider may propose a different plan. For example, if the healthcare system suggests that a plan fails to address a clinical condition, the healthcare provider may propose a different plan. Similarly, if the healthcare system suggests that a plan fails to address a patient's objectives, the healthcare provider may propose a different plan. The new plan may reflect differing objectives of treatment, from either the patient or provider. The healthcare system analyzes the new plan in the same manner as it analyzed the previous plan. Once the patient and provider decide that a plan is acceptable, it may be administered to a patient.

Before being administered, a treatment plan is authorized by the appropriate entities, including a patient or patient's guardian, and an insurance company or other entity responsible for payment of the treatment. A patient agrees to a course of treatment and any associated risks thereof. The treatment plan provided for each patient therefore includes customized patient consent forms, detailing the treatment plan and its associated risks.

After an approved treatment plan has been administered, the healthcare system compares the actual outcomes of treatment to the expected outcomes of treatment to evaluate the effectiveness of the treatment plan (step 208). In this step, the healthcare system provides information about how well a treatment plan met its objectives, the effectiveness of treatment planning decisions, the effectiveness of treatment in preventing additional treatment, and the accuracy of risk assessment. An exemplary patient outcomes assessment report is included in Table 7, below.

The healthcare system computes outcomes assessment data for each group of 200 patients, thereby assisting healthcare providers in tracking their performance on an ongoing basis. Therefore, after evaluating the effectiveness of the treatment plan, the healthcare system determines whether more than 200 patients for a specific healthcare provider have been analyzed by the system (step 210). If so, the healthcare system calculates outcomes assessment data for the healthcare provider using the outcomes assessment data for a provider using the outcomes assessment data for each patient, groups it by percentile, and reports the information to the provider (step 212). Additional details of the outcomes assessment data computed by the healthcare system are described relative to the discussion of FIG. 5, below. An exemplary provider outcomes assessment report is included in Table 8, below. This provider outcomes assessment information may be used to determine a provider's overall standard of care. If less than 200 patients have been analyzed by the system, processing continues to step 202.

The healthcare system periodically adjusts, or updates computed risk values to increase the accuracy of the system's computation of risk values. Risk values are updated by the system for each set of 300 patients. Thus, after performing outcomes assessment, the healthcare system determines whether the next group of 300 patients, regardless of provider, has been analyzed by the system (step 214). If not, processing continues to step 202. Otherwise, the healthcare system uses the patient outcomes assessment information to automatically update, i.e., adjust, the risk value computed during risk assessment (step 216). The risk update process re-calculates a computed risk value. The risk update process re-calculates each patient's computed value of risk to make it consistent with both the actual risk for all patients, based on values derived from the patient and provider outcomes assessment, and the patient's risk as determined by outcomes associated with previous treatment received by that patient. This re-calculation considers the value of risk adjustment factors that represent trends in risk values among all patient. Additional details of the risk adjustment factors are described below relative to the discussion of FIG. 7.

This risk adjustment represents one way the healthcare system evolves over time. For example, during the lifetime of a patient the patient's risk value changes due to changes in both, e.g., the patient's diagnostic information and changes in the risk update factors. By updating the risk value for each patient each time an additional 300 patients receive treatment plans approved by the system, the system increases the accuracy of both the risk update factors and the overall computation of a risk value.

Figure 3:
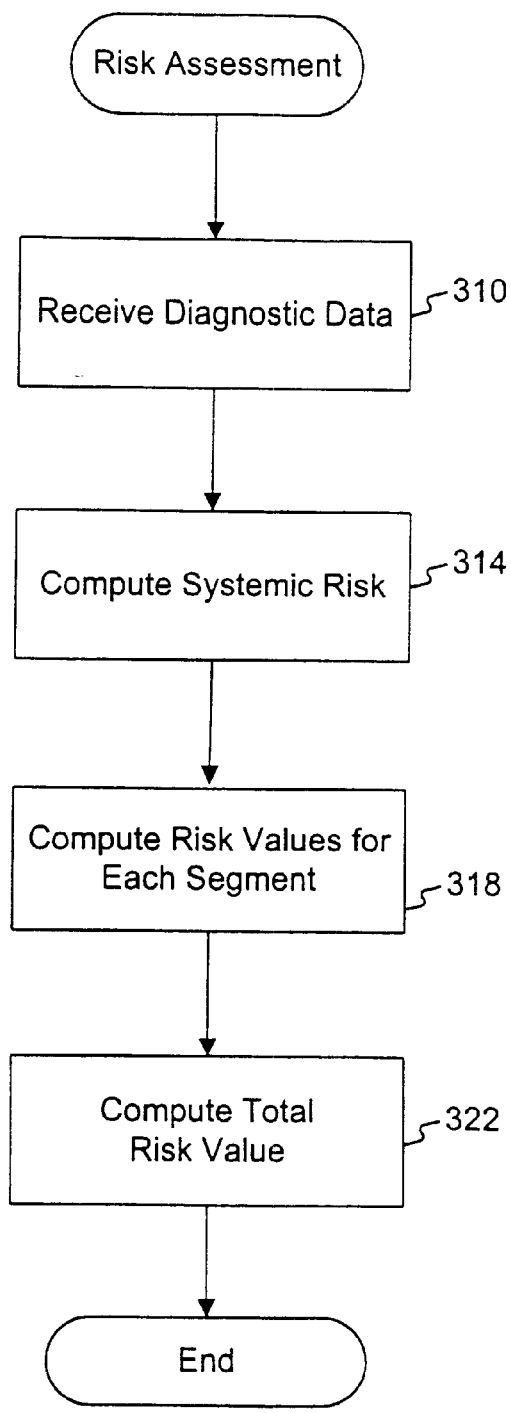
FIG. 3 depicts a flowchart of the steps performed by the healthcare system, depicted in FIG. 1, when performing risk assessment.

FIG. 3 depicts, in greater detail, a flowchart of the steps performed by the healthcare system when performing risk assessment, as described in step 204 of FIG. 2. First, the healthcare system receives from a healthcare provider diagnostic data (step 310). The healthcare system uses a subset of the diagnostic data to compute a patient's risk value by considering the sum of three components of risk, including (1) systemic risk, (2) exposure risk, and (3) experience risk.

The subset of data used to compute risk includes the data determined by scientific analysis to be relevant in assessing a person's risk of contracting a disease, or being responsive to treatment.

Systemic risk reflects a measure of a patient's overall risk and is not related to a particular segment of the mouth, as are exposure and experience risk. The healthcare system computes systemic risk as the product of a pre-defined standard risk value, parental history of periodontitis, patient's history of diabetes, and patient's use of cigarettes, all listed in Table 2 as personal health history information (step 314). The healthcare system converts this computed value to an integer that represents the systemic risk. For example, if the computed value for systemic risk was 19.2 or 19.9, the healthcare system uses 19 as the systemic risk value. The standard risk value used to compute systemic risk is initially set to 15 by the healthcare system.

The healthcare system then calculates exposure and experience risk values for the six segments of the mouth, including (1) maxillary and first and second molars and maxillary first premolars, (2) mandibular first and second molars, (3) maxillary incisors, (4) mandibular incisors, (5) mandibular first and second premolars and maxillary second premolars, and (6) canines (step 318). If no teeth are contained in a segment then the total risk value for that segment is set to zero. The healthcare system's breakdown of risk values by segment allows for precise calculation of risk, thereby supporting targeted treatment planning.

To calculate exposure risk for a segment, the healthcare system first computes, e.g., the sum of the values corresponding to periodontal inflammation, pocket depth multiplied by 2, bone loss multiplied by 4, and mobility times 6. The value for each of these data points may be found in items 19, 20, 21, and 18 of Table 1, respectively. This value ranges between 0 and 13. The healthcare system then converts the value to a 0 to 50 scale by multiplying the computed value by, e.g., 3.84. To this value, the healthcare system then adds e.g., the value of the furcations, item 41 of Table 1, and the value reflecting annual professional cleanings, item 4 of Table 2. This sum represents the exposure risk and is done for each segment. An example that uses this series of calculations to compute an exposure risk value is provided below, relative to the discussion of Table 6B. If the value of the exposure risk is less than 0, the healthcare system uses 0 as the value for exposure risk.

The healthcare system assigns an experience risk value to each segment based on the periodontal breakdown values received as diagnostic data. Specifically, the healthcare system determines this value by counting the number of years since the last entry in Table 1 reflecting pathologic sulcus deeper than 5 mm, item 20, or radiographic evidence of disease, item 21. Table 5 lists an exemplary set of values the healthcare system assigns to different levels of periodontal breakdown.

TABLE 5

| Periodontal Breakdown | Value |
|---|---|
| bone loss has occurred or if bone level maintained < 2 years | 10 |
| bone level maintained > 2 years and < 5 years | 0 |
| bone level maintained > 5 years and < 10 years | −10 |
| bone level maintained ≧ 10 years | −20 |

After determining the exposure and experience risk values for each segment containing teeth, and the systemic risk value of a patient, the healthcare system computes the patient's total risk according to the following formula (step 322):

(systemic risk−|systemic risk|*"sys")+(exposure risk−|exposure risk|*"xpos")+(experience risk−|experience risk|*"xper")+"totalnew" where "sys," "xpos," "xper," and "totalnew" are variables representing risk adjustment factors. Each of these variables is discussed below with respect to FIG. 7, relative to the discussion of updating risk values. If the total risk value is less than 0, the healthcare systems uses 0 for the total risk value.

The healthcare system ranks a computed risk value as low, moderate, or high. The initial value for low risk is 20 or less, moderate risk is between 20 and 40, and high risk is any value greater than 40. The low, moderate and high ranges are updated according to the risk values for all patients considered by the healthcare system as follows: low risk includes values in the bottom 20% of all patients' risk values, moderate risk includes values in the 20–80% range of all patients' computed risk values, and high risk includes values in the upper 20% of all patients' risk values.

Tables 6A and 6B, below, provide values for an exemplary set of risk data that may be processed by the healthcare system. Table 6A reflects personal health history information, i.e., the data used to compute a patient's systemic risk value. By using the formula discussed above the healthcare system computes this patient's systemic risk value as 19.

Table 6B reflects an exemplary set of clinical data for each segment that may be used to compute a patient's exposure and experience risk values. The risk calculation indicates that this patient has a total risk value of 21. The value of 21 is obtained by adding the risk values for the six segments and dividing the sum by the number of segments having a risk score greater than 0. This patient's risk values for each segment are as follows: segment 1—exposure 22, experience 10, total risk 51; segment 2—exposure 7, experience—20, total risk 6; segment 3—exposure 0, experience—20, total risk 0; segment 4—exposure 0, experience—20, total risk 6; segment 5—exposure 7, experience—20, total risk 6; segment 6—exposure 0, experience—20, total risk 0.

TABLE 6A

Personal Health History Information

| Data Point | Response | Value |
|---|---|---|
| parental history of peridontitis | unknown | 1 |
| patient's history of diabetes | none | 1 |
| patient's use of cigarettes | >10 per day | 1.3 |
| number of professional cleanings per year | 2 per year | −4 |

TABLE 6B

| Clinical Data Per Segment Data Point | Segment 1 | Segment 2 | Segment 3 | Segment 4 | Segment 5 | Segment 6 |
|---|---|---|---|---|---|---|
| Number of teeth | 6 | 4 | 4 | 4 | 6 | 4 |
| Presence of Inflammation | 1 | 1 | 0 | 1 | 1 | 1 |
| Pocket Depth ("0" if < 5 mm; "1" if > 5 mm) | 1 | 1 | 0 | 0 | 1 | 0 |
| Bone Loss ("0" if < 2 mm; "1" if > 2 mm) | 1 | 0 | 0 | 0 | 0 | 0 |
| Existence of Mobility ("0" if < 1 degree "1"if > 1 degree) | 0 | 0 | 0 | 0 | 0 | 0 |
| Existence of Furcations ("0" if none; "0" if < grade 1, "10" if > grade 1) | 0 | 0 | 0 | 0 | 0 | 0 |

TABLE 6B-continued

| Clinical Data Per Segment Data Point | Segment 1 | Segment 2 | Segment 3 | Segment 4 | Segment 5 | Segment 6 |
|---|---|---|---|---|---|---|
| Peridontal Breakdown ("0" if bone loss or bone maintained < 2 years; "1" if bone level > 2 years + < 5 years; "2" if bone level > 5 years + < 10 years; "3" if bone level > 10 years | 0 | 3 | 3 | 3 | 3 | 3 |

Figure 4:
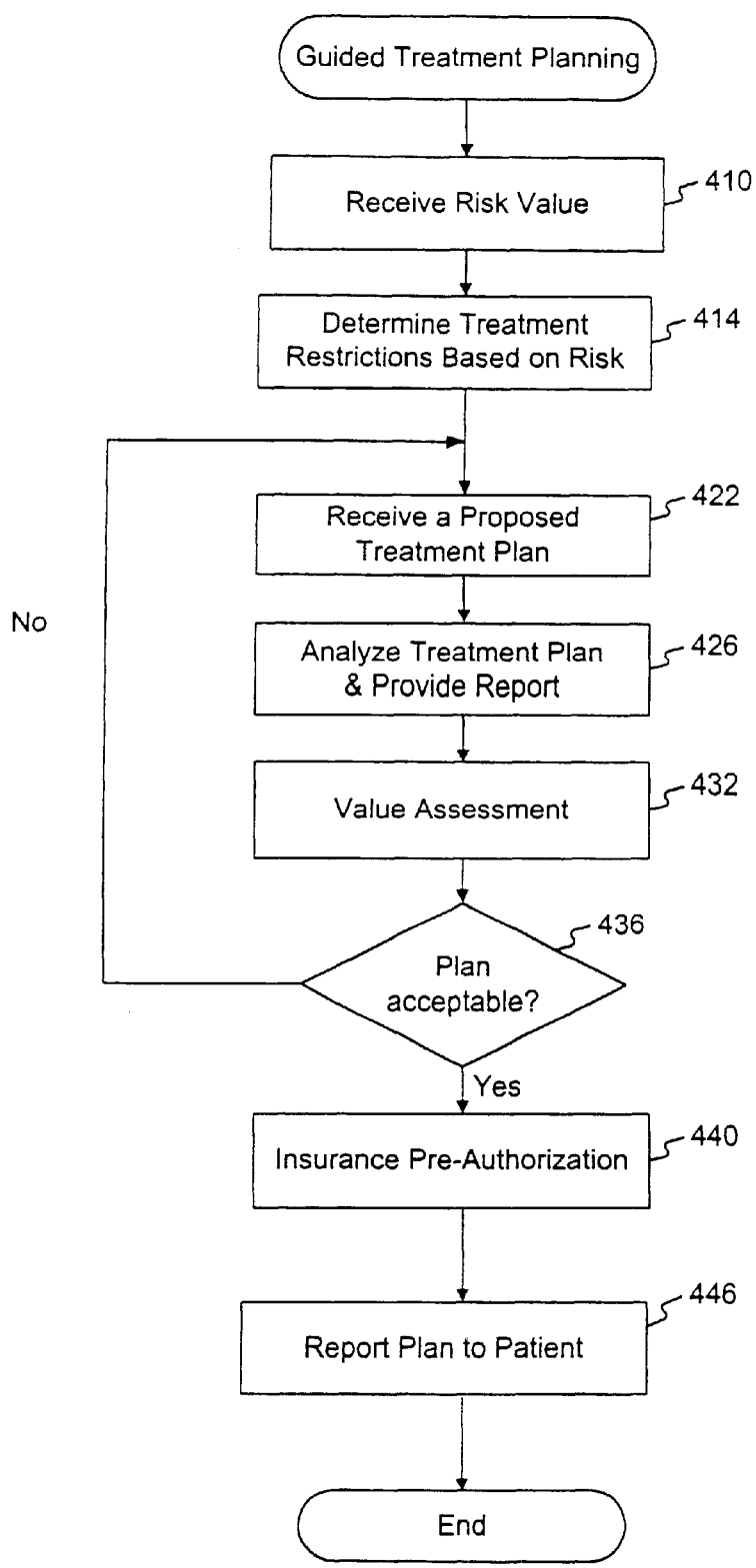
FIG. 4 depicts a flowchart of the steps performed by the healthcare system, depicted in FIG. 1, when performing guided treatment planning.

FIG. 4 depicts, in greater detail, a flowchart of the steps performed by the healthcare system when performing guided treatment planning, as described relative to step 206 of FIG. 2. First, the healthcare system receives a risk value (step 410). A healthcare provider uses the risk value e.g., to determine a treatment plan. The risk value is used in this process to determine the best treatment according to both the patient's diagnostic data and the computed risk value. Treatment restrictions refer to limitations on treatment based on the patient's risk value, and considering the patient's diagnostic information. A healthcare provider considers treatment restrictions when developing a treatment plan (step 414).

The healthcare provider then provides a treatment plan, reflecting treatment restrictions, to the healthcare system (step 422). Continuing with the exemplary set of risk data listed in Tables 6A and 6B above, suppose the dentist also collects the following diagnostic data during the examination:

(1) clinical conditions—heavily filled teeth 2, 3, and 4; root proximity associated with teeth 2 and 3; and generalized periodontal breakdown including pocket depth measurements greater than 5 mm (Table 1, items 6, 17, 19, 20, 21, and 26);

(2) patient objectives—to fix dental problems while avoiding extraction of any teeth (Table 3, items 4 and 14)

(3) provider objectives—to satisfy patient objectives; eliminate clinical signs of inflammation; reduce probing depths to less than 5 mm; and create restorations having marginal integrity, physiologic form and proper contacts (Table 3, items 24, 27, 28, 35, 36, and 37);

(4) adverse factors—susceptibility to periodontal disease; limited embrasure space; root proximity; and bone architecture of the segment including teeth 2 and 3 (Table 4, Items 10, 21, 22, and 26).

The dentist may propose the following treatment plan: root planing for all teeth, osseous surgery for the segment including teeth 2–5, endodontics for tooth 3, and crowns for teeth 2–4.

After, the provider proposes a plan, the healthcare system analyzes the plan and provides a report of its analysis (step 426). The analysis considers the feasibility of the treatment plan proposed by the provider, given the limitations associated with the patient's risk value, insurance coverage, and diagnostic information. The system ensures that objectives correspond to clinical conditions and vice versa. It also ensures that all clinical conditions are addressed in the treatment plan. The healthcare system also identifies additional adverse affects associated with a proposed treatment plan. Finally, the healthcare system provides information about the patient's and provider's prior predictive history regarding effectiveness, adverse effects, and longevity. This analysis information may be used to help a patient or provider adjust their objectives in order to adopt a treatment plan that is likely to yield the most effective long-term impact at the lowest cost. The healthcare system then prints a detailed report, analyzing the plan. The report lists the diagnostic information, adverse effects, estimated cost, and predictions regarding treatment effectiveness, adverse effects, longevity, and urgency of treatment.

Continuing further with the example, suppose the healthcare system determines that the patient's insurance company would not approve a bone graft procedure because of the patient's moderate risk score. The healthcare system provides a report indicating reasons why the proposed treatment may not be the most appropriate treatment. For example, the report indicates the adverse factors that reduce the likelihood of success of the osseous surgery and crown procedures. It also indicates that although root planning was done twice in the last six years, neither the surgery nor the crowns were done in the sites listed. The report may further indicate that the proposed treatment plan fails to address a root proximity condition and that the proposed endodontic treatment does not relate to a clinical condition. The report may further identify additional potential adverse effects of the proposed treatment plan to include pulpitis, thermal sensitivity, swelling, or infection, and an increased susceptibility to caries and periodontal disease.

After reviewing the report, if the patient and provider decide that the plan is not acceptable, they may change their objectives and develop a new treatment plan. Suppose the new objectives add prevention (objective 5), including a minimization of cost for future treatment (objective 9), and eliminate the avoidance of tooth extraction (objective 14). The new treatment plan proposes extracting tooth 3 and performing a prosthetic replacement with a three-unit fixed bridge. The healthcare system analyzes the new plan and provides a new report. After reviewing the report of the most recent proposed treatment plan, the patient and doctor tentatively agree that the plan is acceptable in meeting the objectives of care.

After reviewing the healthcare system's analysis of a plan, a healthcare provider predicts the effectiveness of the treatment plan by answering value assessment questions (step 432). The term "value assessment" refers to data indicating a provider's predictions about a treatment plan.

During value assessment the healthcare system receives input from a healthcare provider indicating the provider's predictions regarding the outcomes of the proposed treatment, including urgency, longevity, adverse effects, and effectiveness. Urgency reflects the length of time (in years) treatment may be postponed before the proposed treatment plan becomes invalid, or treatment predictability reduces. Longevity reflects the probability that treatment will last for a specified time period (in years) before additional treatment is needed. Adverse effects reflects the probability that treatment not included in the proposed treatment plan will be needed because the effects of treatment contribute to a new condition. Effectiveness reflects the probability that treatment will result in meeting the objectives of care. The healthcare system displays a value assessment report that includes the objectives of treatment, proposed treatment plan, the predictive value assessment values, and the cost of the plan.

After a provider makes predictions about the plan through the value assessment process, the patient and provider determine whether the plan is acceptable (step 436). A plan may be considered acceptable if, for example, it meets the patient and provider objectives of treatment. If the plan is not acceptable, processing continues to step 422; otherwise, processing continues to step 440.

Once the patient and provider agree upon a treatment plan, the plan, along with information related to a patient's symptoms and an analysis of the plan is analyzed by the healthcare system for insurance company pre-authorization of payment (step 440). The pre-authorization may be done local to the healthcare server. The server contains a database of authorized treatments for a condition, given a specified level of risk and a set of diagnostic information. Once a plan has been pre-authorized, the healthcare system provides a report of the plan, along with a customized consent form, for the patient to review and sign upon acceptance (step 446).

During treatment, a healthcare provider reports to the healthcare system all treatment administered to a patient. This information is maintained by the system and referred to as "treatment records."

Figure 5:
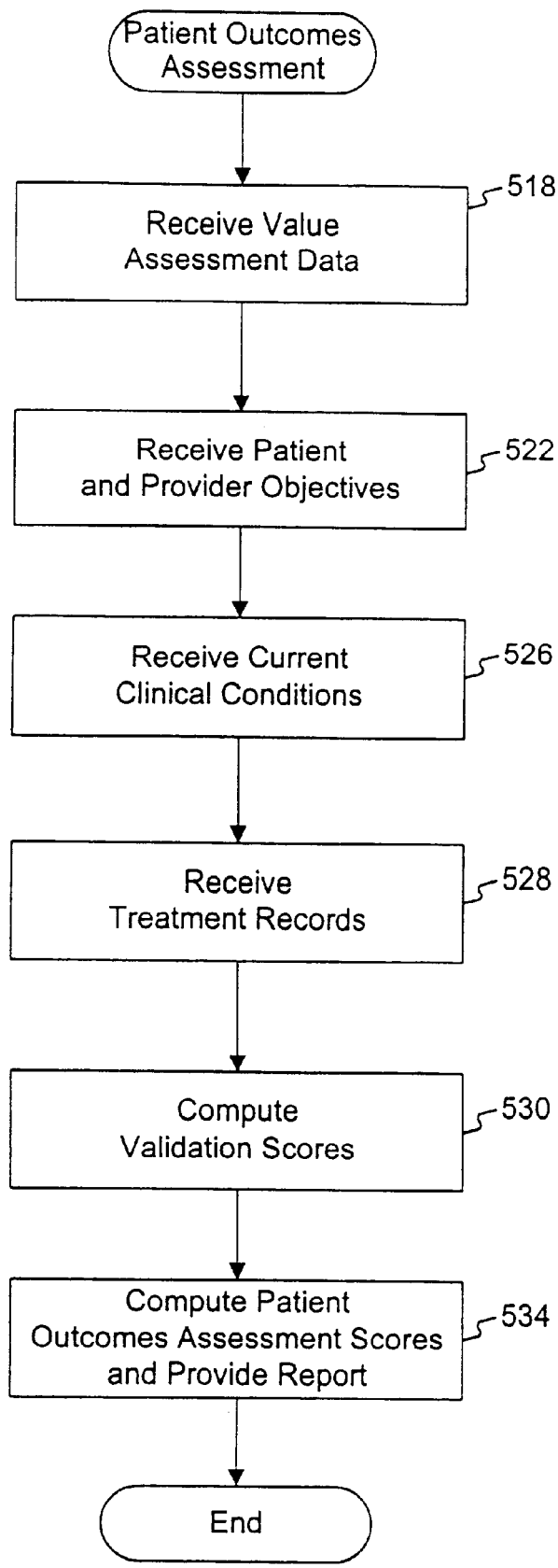
FIG. 5 depicts a flowchart of the steps performed by the healthcare system, depicted in FIG. 1, when performing assessment of patient outcomes.

FIG. 5 depicts, in greater detail, a flowchart of the steps performed by the healthcare system when performing patient outcomes assessment, as described relative to step 208 of FIG. 2. A healthcare provider may request an outcomes assessment report, shown below in Table 7, on a per-patient basis, as desired. An outcomes assessment report provides outcomes assessment data that may be useful to a patient or a provider in determining the effectiveness of a treatment plan. Generally, an outcomes assessment is most valuable if done 1–2 years after a patient has received treatment.

First, the healthcare system receives value assessment information from a provider (step 518). As discussed above, relative to the discussion of FIG. 4, the value assessment data collected by the healthcare system corresponds to data reflecting the following: (1) the probability that a treatment plan will meet the objectives of care, (2) the probability that a treatment plan will yield the need for subsequent treatment for the same or a related condition, and (3) the expected length of time the treatment will last. After receiving the value assessment data, the healthcare system receives updated information reflecting whether patient and provider objectives, listed in Table 3, were met (step 522). For each objective listed in Table 3 corresponding to an affirmative response as indicated in a treatment plan that was approved by a patient and a healthcare provider, the patient (or provider) indicates whether treatment did or did not meet the objective; the patient (or provider) may also indicate an "unsure" response. Each of the "yes," "no," and "unsure" responses is assigned a value of, e.g., "1." The healthcare system calculates the sum of the "yes," "no," and "unsure" values and divides the sum for each category by the sum of the total initial "yes," "no," and "unsure" values.

The healthcare system then receives updated clinical information, listed in Table 1, reflecting a patient's current condition (step 526). The healthcare system captures this information during outcomes assessment to track a patient's progress. Ideally, a patient's clinical conditions, reported during outcomes assessment, will not be the same as the clinical conditions that fed into a treatment plan.

Next, the healthcare system receives information corresponding to treatment records (step 528). The treatment records include a comprehensive listing of treatment received by a particular patient. Each time a provider administers treatment to a patient, the treatment record for that patient is updated.

After collecting the data related to patient and provider objectives, patient clinical conditions, and treatment records, the healthcare system computes a validation score, reflecting the healthcare system's assessment of the accuracy of the data collected for a subset of the objectives, for example, 4–5, 15–17, 22–24, 26–28, 30–32, and 35–37 listed in Table 3 (step 530). The validation score is computed by a validation procedure that determines whether patient and provider responses are consistent. The validation procedure compares data corresponding to (1) the clinical conditions at the time of outcomes assessment, (2) the treatment provided, as reported by a provider during treatment, and (3) values representing assessment scores of the objectives listed in Table 2 and determined in step 518 above. All of the relevant objectives are given initial validation scores of "zero." If the patient or provider outcomes assessment value for a particular objective corresponds to "unsure" or "no," the healthcare system assigns that objective a validation score of negative one; if the outcomes assessment value for a particular objective is "yes," then the system assigns that objective a validation score of positive one. For example, if all planned treatment was administered to a patient then the validation score corresponds to plus one; if all planned treatment was not administered, the validation score corresponds to negative one.

Once the healthcare system determines a validation score for each objective, it computes the sum of the validation scores and divides the sum by the number of validation scores having a value of either positive one or negative one, to convert the scores to a range between negative one and positive one.

The system then computes the other outcomes assessment scores and provides a report of the values (step 534). The outcomes assessment report provides information reflecting how the actual outcomes of a treatment plan compare to the expected outcomes of the plan. Table 7 lists an exemplary outcomes assessment report provided by the healthcare system. Items 8a–8c of Table 7 are computed as the sum of the number of periodontal surgical procedures for each tooth site, less 1 if the number of procedures is greater than 0. Item 8b represents this value, based on the number of periodontal procedures performed over the previous 10 years. Item 8c represents this value based on the numbers of periodontal procedures performed over the previous 5 years. Similarly, items 9a–9c are computed as the sum of the number of restorative and prosthetic treatments performed less 1 (if the number is greater than 0), in total, during the previous 10 years, and during the previous 5 years, respectively.

Items 12, 13, and 14 reflect aspects of a healthcare provider's assessment of a proposed treatment plan. Item 12 reflects a provider's assessment of how well a treatment plan will meet the objectives of care. The healthcare provider inputs this information in the form of a percentage. An exemplary set of values may be assigned as follows:

"1" if 85% or more of all objectives have an assessment of "yes" (Table 7, item 1) and the probability of a treatment plan meeting the objectives of care is moderate or low.

"0" if 85% or more of all objectives have an assessment of "yes" (Table 7, item 1) and the probability of a treatment plan meeting the objectives of care is very high or low; or, if 75% –85% of all objectives have an assessment of "yes" and the probability of a treatment plan meeting the objectives of care is high; or, if 65–85% of all objectives have an assessment of "yes" and the probability of a treatment plan meeting the objectives of care is moderate.

"–1" in all other situations.

Item 13 reflects the probability that a treatment plan will yield a need for subsequent treatment of the same or a related condition. The values for this data point may be determined as follows:

"1" if the value assessment information provided by a healthcare provider (in step 518 of FIG. 5) is greater than 25% and no treatment was needed.

"0" if the value assessment information provided by a healthcare provider (in step 518 of FIG. 5) is between 10% and 25% and no treatment was needed; or, if the value assessment information provided by a healthcare provider (in step 518 of FIG. 5) is greater than 25% and treatment was needed.

"−1" in all other situations.

Item 14 reflects a healthcare provider's assessment of the value reflecting the expected length of time treatment will last (i.e. predictive longevity of treatment, entered in step 512 of FIG. 5). Item 14 also considers the value of repeat periodontal surgical procedures during a 5-year time period (Table 7, Item 8c). The values for item 14 may be calculated, for example, as follows:

"−1" if the healthcare provider is unsure whether treatment lasted as long as expected;

"0" if the healthcare provider believes treatment will last as long as initially expected, the predictive longevity of treatment is less than 5 years, and the value for repeat periodontal surgical procedures is greater than 0;

"1" if the healthcare provider believes treatment will last as long as initially expected, the predictive longevity of treatment is less than 5 years, and the value for repeat periodontal surgical procedures is 0;

"−1" if the healthcare provider believes treatment will last as long as initially expected, the predictive longevity of treatment is greater than 5 years, and the value for repeat periodontal surgical procedures is greater than 0;

"0" if the healthcare provider believes treatment will last as long as initially expected, the predictive longevity of treatment is greater than 5 years and the value for repeat periodontal surgical procedures is 0;

"1" if the healthcare provider believes treatment will last as long as initially expected and the predictive longevity of treatment is greater than 10 years;

"−1" if the healthcare provider believes that treatment will last as long as initially expected and the value of the predictive longevity of treatment is "unsure";

"1" if the healthcare provider believes that treatment will not last as long as initially expected and the predictive longevity of treatment is less than 5 years; and "−1" if the healthcare provider believes that treatment will last as long as initially expected and the predictive longevity of treatment is not less than 5 years.

TABLE 7

PATIENT OUTCOMES ASSESSMENT SCORE

| NO. | DESCRIPTION | VALUE |
|---|---|---|
| 1 | Percentage of all objectives (yes) with an assessment of yes. Range 0–100%. | % |
| 2 | Percentage of all objectives (no) with an assessment of no. Range 0–100%. | % |
| 3 | Percentage of all objectives (unsure) with an assessment of unsure. Range 0–100%. | % |
| 4 | Percentage of all patient objectives (#1–14 - yes) with an assessment of yes. Range 0–100%. | % |
| 5 | Percentage of all patient objectives (#1–14 - no) with an assessment of no. Range 0–100%. | % |
| 6 | Percentage of all patient objectives (#1–14 - unsure) with an assessment of unsure. Range 0–100%. | % |
| 7 | Validation score. The sum of the validation scores divided by the sum of the count of scores equal to 1 and the count of scores equal to −1. Range −1 to +1. | # |

TABLE 7-continued

PATIENT OUTCOMES ASSESSMENT SCORE

| NO. | DESCRIPTION | VALUE |
|---|---|---|
| 8a | Total Periodontal re-treatment score. | # |
| 8b | Periodontal re-treatment score - last 10 years | # |
| 8c | Periodontal re-treatment score - last 5 years | # |
| 9a | Total Restorative and prosthetic treatment time interval score. | # |
| 9b | Restorative and prosthetic treatment time interval score - last 10 years. | # |
| 9c | Restorative and prosthetic treatment time interval score - last 5 years. | # |
| 10 | Questionable treatment choice score. The dollar amount spent for sites that had endodontic, prosthodontic or bone graft treatment prior to extraction of a tooth. This score is the sum of dollar amount for all sites. | $ |
| 11 | Questionable treatment choice site list. The sites that are included in the questionable treatment choice score. | site list |
| 12 | Predictive history on effectiveness. Values are −1, 0, +1 with −1 = outcome worse than expected; 0 = outcome as expected; +1 = outcome better than expected. | # |
| 13 | Predictive history on adverse effects. Values are −1, 0, +1 with −1 = outcome worse than expected; 0 = outcome as expected; +1 = outcome better than expected. | # |
| 14 | Predictive history on longevity. Values are −1, 0, +1 with −1 = outcome worse than expected; 0 = outcome as expected; +1 = outcome better than expected. | # |
| 15 | Composite predictive history. Sum of values for items 12, 13 and 14 above. Value range is −3 to +3 with < 0 = outcomes fell short of predictions; = 0, outcomes matched predictions; > 0 outcomes exceeded predictions. | # |

Figure 6:
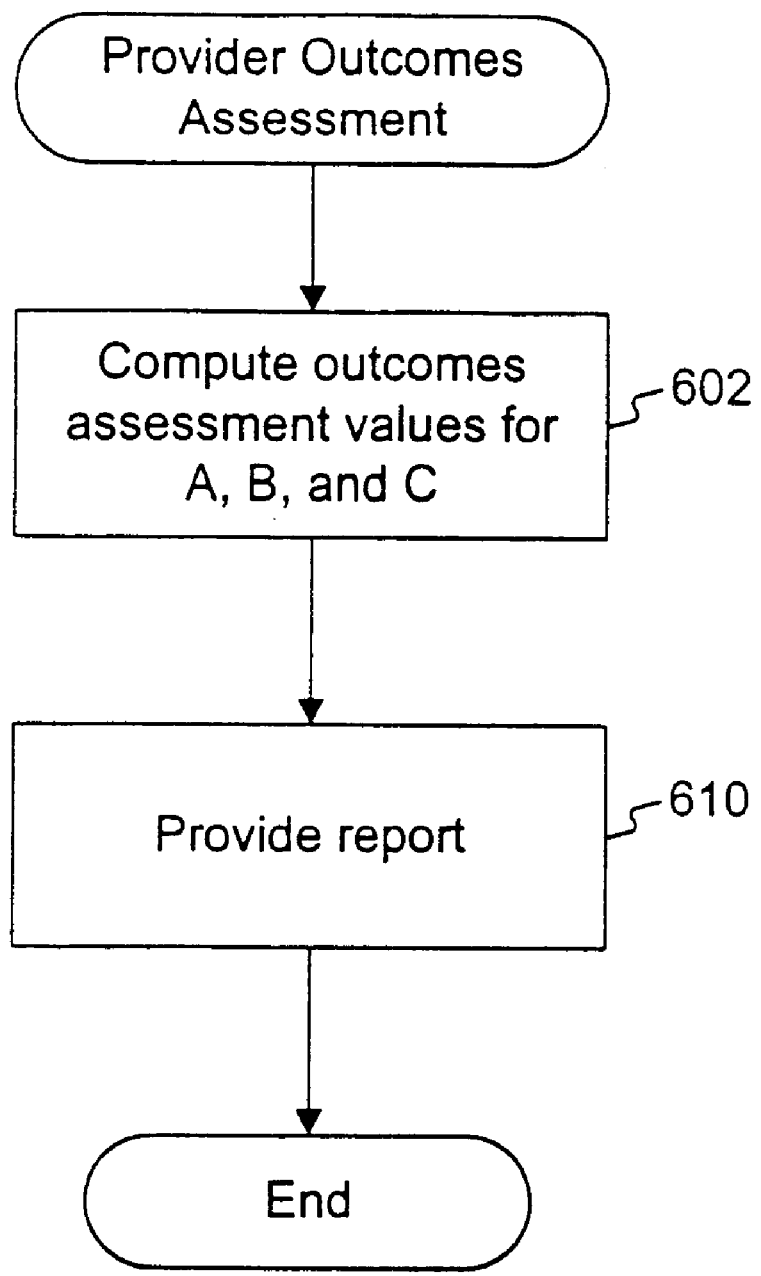
FIG. 6 depicts a flowchart of the steps performed by the healthcare system, depicted in FIG. 1, when performing assessment of provider outcomes.

FIG. 6 depicts, in greater detail, a flowchart of the steps performed by the healthcare system when performing provider outcomes assessment, as described relative to step 212 of FIG. 2. The healthcare system groups the patient outcomes assessment values corresponding to items 1–6 and 8a–9c, shown above in Table 7, by percentile range (step 602). The percentile ranges correspond to the groupings marked "A," "B," and "C" in Table 8, below. Value "A" represents the 50$^{th}$ percentile; value "B" represents the 70$^{th}$ percentile; and value "C" represents the 90$^{th}$ percentile. The healthcare system provides a report of the computed values to the relevant healthcare provider (step 610). This information reflects a provider's effectiveness as determined during patient outcomes assessment.

For items 7 and 12–15, the healthcare system computes the percentage of outcomes assessment data values falling in the ranges specified in Table 8. For example, "Value A" of item 7 corresponds to the sum of all validation score values that are less than zero, divided by the sum of all validation score values.

TABLE 8

PROVIDER OUTCOMES ASSESSMENT DATABASE

| POAS Item # | Value A | Value B | Value C |
|---|---|---|---|
| 1 | 50$^{th}$ percentile | 70$^{th}$ percentile | 90$^{th}$ percentile |
| 2 | 50$^{th}$ percentile | 70$^{th}$ percentile | 90$^{th}$ percentile |
| 3 | 50$^{th}$ percentile | 70$^{th}$ percentile | 90$^{th}$ percentile |
| 4 | 50$^{th}$ percentile | 70$^{th}$ percentile | 90$^{th}$ percentile |
| 5 | 50$^{th}$ percentile | 70$^{th}$ percentile | 90$^{th}$ percentile |
| 6 | 50$^{th}$ percentile | 70$^{th}$ percentile | 90$^{th}$ percentile |
| 7 | % < 0 | % = 0 | % > 0 |
| 8a | 50$^{th}$ percentile | 70$^{th}$ percentile | 90$^{th}$ percentile |
| 8b | 50$^{th}$ percentile | 70$^{th}$ percentile | 90$^{th}$ percentile |
| 8c | 50$^{th}$ percentile | 70$^{th}$ percentile | 90$^{th}$ percentile |

TABLE 8-continued

PROVIDER OUTCOMES ASSESSMENT DATABASE

| POAS Item # | Value A | Value B | Value C |
| --- | --- | --- | --- |
| 9a | 50$^{th}$ percentile | 70$^{th}$ percentile | 90$^{th}$ percentile |
| 9b | 50$^{th}$ percentile | 70$^{th}$ percentile | 90$^{th}$ percentile |
| 9c | 50$^{th}$ percentile | 70$^{th}$ percentile | 90$^{th}$ percentile |
| 12 | % (−1) | % (0) | % (+1) |
| 13 | % (−1) | % (0) | % (+1) |
| 14 | % (−1) | % (0) | % (+1) |
| 15 | % < 0 | % = 0 | % > 0 |

The healthcare system tabulates provider outcomes assessment information in two categories (1) for each set of 200 patients associated with a provider, and (2) for all patients associated with a provider. If a provider has more than 200 patients, each set of 200 patients' outcomes assessment values will be contained in a separate table. Thus, if a provider has 601 patients, four tables are computed during provider outcomes assessment: one table is computed for each group of 200 (including data for patients 1–600), and one table is computed for the entire group of 600. Data related to patient 601 is contained in a provider outcomes assessment report done after the provider treats an additional 199 patients.

Figure 7:
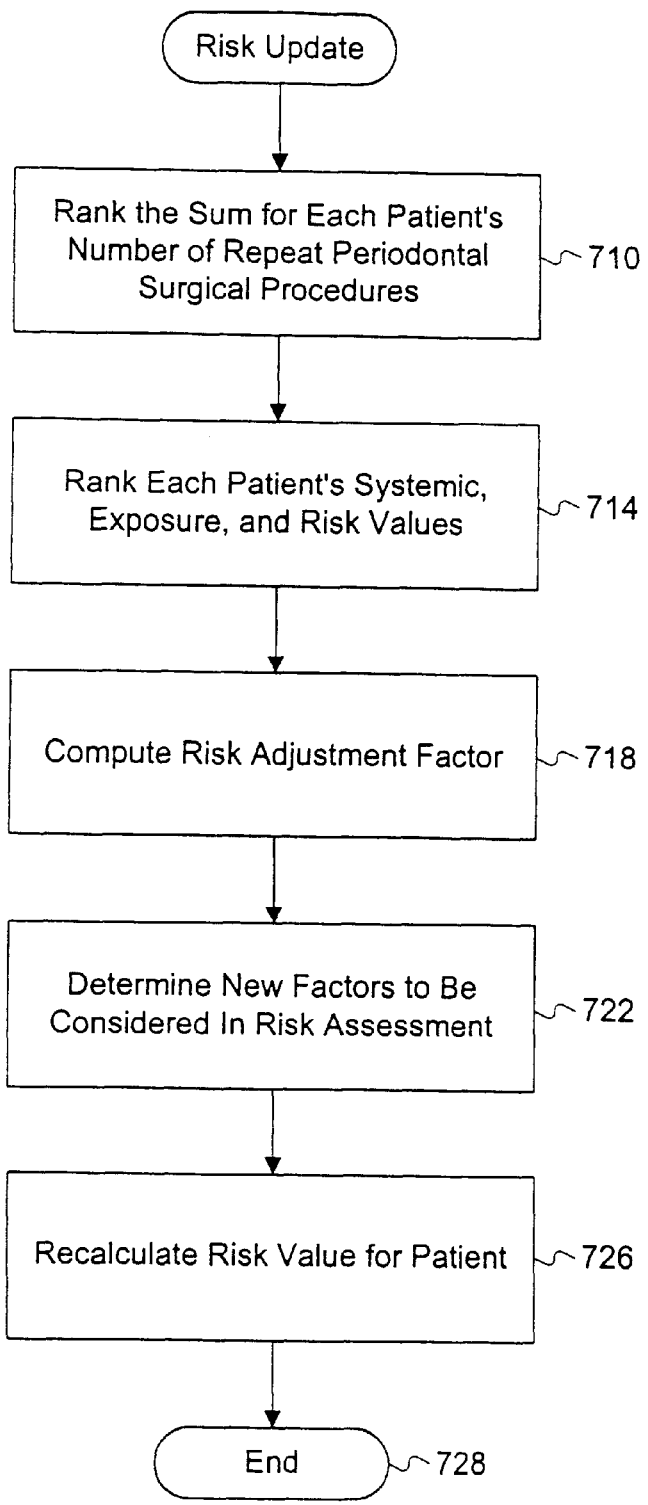
FIG. 7 depicts a flowchart of the steps performed by the healthcare system, depicted in FIG. 1, when updating a computed risk value.

FIG. 7 depicts, in greater detail, a flowchart of the steps performed by the healthcare system when it adjusts a computed risk value as described in step 216 of FIG. 2. For each patient having a risk value and outcomes assessment data, the healthcare system updates, or adjusts the patient's risk value by: (1) computing an adjustment factor for each of the three categories, systemic, exposure, and experience risk by comparing the previously computed risk values, which are predictions, with quantified values reflecting actual occurrences at sites that required more than one surgical treatment (item 8a of Table 7), and (2) adding quantified values for new factors to be included in the computation of a risk value. Values of the diagnostic data, including patient health history, drugs and medications, and laboratory reports may all be considered in identifying new factors to include in the computation of a risk value.

To compute a risk adjustment factor, the healthcare system first ranks the sum of each patient's number of repeat periodontal surgical procedures (step 710). To rank the repeat periodontal surgical procedures, the healthcare system classifies the repeat periodontal surgical procedure values for each patient listed in the database by deciles, or groups of 10 percentiles. Next the healthcare system ranks the systemic, exposure, and experience risk values for each patient in terms of deciles, or groups of 10 percentiles (step 714). Then, the healthcare system computes the risk adjustment factors for systemic risk, "sys," exposure risk, "xpos," and experience risk, "xper," by subtracting the rank for a patient's repeat periodontal surgical procedure value from the rank for the patient's risk value for each category of risk (systemic, exposure, or experience), and converting it to a number ranging from (−0.3) to (+0.3) (step 718). This process must be done three times for each patient to compute "sys," "xper," and "xpos." To convert the updated value to a range between (−0.3) and (+0.3), the healthcare system may, for example, perform the following steps: subtract the rank for a patient's repeat periodontal surgical procedure value from the rank for the patient's risk value for each category of risk (systemic, exposure, or experience), change the sign of the number to positive (unless it is already positive), add 1 to the number to change the range from 1–10, multiply the number by 0.3 to change the range from 0.3 to 3, round the number up to change the range from 1 to 3, divide by 10 to change the range from 0.1 to 0.3, and adjust the sign of the update value, changing the range from −0.3 to +0.3. This positive sign adjustment is the positive or negative sign of the value of subtracting the rank for a patient's repeat periodontal surgical procedure value from the rank for the patient's risk value.

The healthcare system further adjusts computed risk values by identifying and quantifying additional factors to be included in computation of a risk value (step 722). To identify additional factors to be included in the computation of a risk value, the healthcare system first generates a frequency distribution of positive occurrences for the diagnostic data collected. "Positive occurrence" refers to a patient having a designated disease or laboratory value, or taking a specified drug. The healthcare system creates this frequency distribution for three categories of patients, including: (1) all patients, (2) high risk patients, and (3) low risk patients. The healthcare system defines patients having risk values in the upper 20% of the range of total risk values as high risk patients, and patients having risk values in the lower 20% of the range of total risk values as low risk patients. The healthcare system compares the frequency distribution for these categories as follows: If the value of a data point for a patient having a high risk has a frequency of occurrence of more than twice the frequency of occurrence of that data point for all patients in the patient database, and if the value of a data point for a patient having a low risk has a frequency of occurrence of less than twice the frequency for all patients in the patient database, then the healthcare system identifies the data point as an additional factor to be considered in computing a risk value and quantifies the value as (+2). On the other hand, if the value of a data point for a patient having a high risk has a frequency of occurrence of less than twice the frequency of occurrence of the same data point for all patients in the patient database, and if the value of a data point for a patient having a low risk has a frequency of occurrence of more than twice the frequency for all patients in the database, then the healthcare system identifies the data point as an additional factor to be considered in computing a risk value and quantifies the value as (−2). The healthcare system repeats this process of identifying and quantifying additional factors to include in computing a risk value for each combination of two data points of items of diagnostic data included in the frequency distributions of high and low risk patients. The newly identified factors and their values are maintained in the patient database. The sum of the newly identified factors corresponds to the variable "totalnew", discussed above relative to FIG. 3 and the discussion of computing a risk value.

After the healthcare system computes the risk adjustment factors and identifies additional factors to consider in computing a risk value, it recalculates a patient's total risk value by plugging the risk update factors and "totalnew" into the equation used to compute total risk (step 726). More specifically, the healthcare system recalculates a patient's total risk value by multiplying the previously computed values of systemic, exposure and experience risk by the appropriate update values, determining the sum of those values, and adding to it, the sum of "totalnew."

Conclusion

By considering various factors impacting a patient's risk of both developing a disease and responding to treatment, a healthcare system consistent with the present invention assists a healthcare provider in making more effective healthcare decisions, thereby decreasing both economic and non-economic costs of healthcare to patients and insurance companies.

Additionally, by maintaining a database of patient records and analysis information related to treatment and associated results, the healthcare system supports uniform and higher quality healthcare. The data maintained by the healthcare system may be used for scientific study and analysis purposes, making it possible to trace the evolution of a patient's health by analyzing data maintained at a central repository.

Although methods and systems consistent with the present invention have been described with reference to an embodiment thereof, those skilled in the art will know of various changes in form and detail which may be made without departing from the spirit and scope of the invention as described in the appended claims and the full scope of their equivalents.

What is claimed is:

1. A method in a data processing system for determining an appropriate treatment for a patient, comprising the steps of:

receiving diagnostic data indicating a current state of a patient;

receiving data reflecting treatment objectives of the patient and the provider indicating a preferred treatment outcome;

receiving a plurality of treatment plans for the current state and for preventing the patient from developing a disease;

computing first risk values for the patient associated with respective ones of the treatment plans, each one of the first risk values being based on a subset of the diagnostic data and indicating a likelihood of the patient developing the disease if the associated treatment plan is followed;

computing second risk values for the patient associated with respective ones of the treatment plans, each one of the second risk values being based on a subset of the diagnostic data and indicating a likelihod of the patient being responsive to treatment of the current state if the associated treatment plan is followed;

receiving an indication of a selected one of the treatment plans;

receiving an indication of a degree of success of the selected treatment plan in treating the current state and preventing the development of the disease;

comparing the degree of success with the treatment objectives to assess the effectiveness of the selected treatment plan; and adjusting the computed first and second risk values for the selected treatment plan based on the effectiveness to increase an accuracy in determining the appropriate treatment.

2. The method of claim 1 further including the step of obtaining insurance pre-authorization for one of the treatment plans based on the risk value therefor.

3. The method of claim 1 wherein the disease under examination is multi-factorial.

4. The method of claim 1 further comprising adjusting the computed risk value consistent with outcomes of prior treatment.

5. A method in a data processing system for determining an appropriate treatment for a current state of a patient, comprising the steps of:

receiving diagnostic data reflecting the current state of the patient and treatment objectives for the patient;

computing a risk value reflecting a likelihood of the patient developing a disease induced by treatment of the current state based on a subset of the diagnostic data;

receiving a proposed treatment plan for the current state that reflects the computed risk value and the treatment objectives; and analyzing the proposed treatment plan to determine a likelihood that the proposed treatment plan will successfully treat the current state, prevent the patient from developing the disease induced by the treatment, and satisfy the treatment objectives.

6. The method of claim 5 wherein the analyzing step includes:

receiving patient and provider objectives of treatment indicating a preferred treatment outcome; and determining whether the proposed treatment plan is consistent with the patient and the provider objectives of treatment.

7. The method of claim 5 wherein the analyzing step includes determining whether the proposed treatment plan is appropriate for the diagnostic data.

8. The method of claim 5 wherein the analyzing step includes determining whether the proposed treatment plan is appropriate based upon prior treatment provided.

9. The method of claim 5 further including the step of adjusting the computed risk value based on prior outcomes of treatment to increase an accuracy in determining the appropriate treatment.

10. The method of claim 5 wherein the step of receiving includes accessing the diagnostic data from a remote location.

11. The method of claim 5 wherein the computing step includes adjusting the risk value based on prior outcomes of treatment to increase an accuracy in determining the appropriate treatment.

12. The method of claim 5 further including the step of transmitting the computed risk value to an external source for pre-authorization of a treatment for the patient.

13. The method of claim 12 wherein the transmitting step includes transmitting the computed risk value to an insurance company.

14. The method of claim 12 wherein the transmitting step includes transmitting the computed risk value to an organization that makes policy decisions pertaining to healthcare benefits.

15. A method in a data processing system for determining an appropriate treatment for a current state of a patient, comprising the steps of:

receiving diagnostic data reflecting the current state of the patient;

computing a risk value reflecting a likelihood of the patient being responsive to the treatment of the current state based on a subset of the diagnostic data;

receiving a proposed treatment plan for the current state that reflects the computed risk value; and analyzing the proposed treatment plan to determine a likelihood that the proposed treatment plan will successfully treat the current state.

16. The method of claim 15 wherein the analyzing step includes: receiving patient and provider objectives of treatment indicating a preferred treatment outcome; and determining whether the proposed treatment plan is consistent with the patient and the provider objectives of treatment.

17. The method of claim 15 wherein the analyzing step includes determining whether the treatment plan is appropriate for the diagnostic data.

18. The method of claim 15 wherein the analyzing step includes determining whether the proposed treatment plan is appropriate based upon prior treatment provided.

19. The method of claim 15 further including the step of adjusting the compound risk value based on prior outcomes of treatment to increase an accuracy in determining the appropriate treatment.

20. The method of claim 15 wherein the receiving step includes accessing the diagnostic data from a remote location.

21. The method of claim 15 wherein the computing step includes adjusting the risk value based on prior outcomes of treatment to increase an accuracy in determining the appropriate treatment.

22. The method of claim 15 further including the step of transmitting the computed risk value to an external source for pre-authorization of a treatment for the patient.

23. The method of claim 22 wherein the transmitting step includes transmitting the computed risk value to an insurance company.

24. The method of claim 22 wherein the transmitting step includes transmitting the computed risk value to an organization that makes policy decisions pertaining to healthcare benefits.

25. The method of claim 15 further comprising analyzing the proposed treatment plan to determine a likelihood that the proposed treatment plan will prevent the patient from developing a diseased induced by the proposed treatment plan.

26. A data processing system including a client and a healthcare server, comprising;
a storage device including patient health information that includes data reflecting a current state of the patient and treatment objectives for the patient;
a memory including administrative software and a healthcare system that (1) computes a risk value based on diagnostic data, the risk value reflecting a likelihood of the patient developing a disease induced by treatment of the current state, and (2) that analyzes a proposed treatment plan for the current state to determine a likelihood that the proposed treatment plan will successfully treat the current state, prevent the patient from developing the disease induced by the treatment, and satisfy the treatment objectives; and
at least one processor for executing the healthcare system and the administrative software.

27. A data processing system including a client and a healthcare server, comprising:
means for receiving diagnostic data reflecting a patient's current state treatment objectives for the patient;
means for computing a risk value based on a subset of the diagnostic data, the risk value reflecting a likelihood of the patient developing a disease induced by treatment of the current state;
means for receiving a proposed treatment plan for the current state that reflects the computed risk value and the treatment objectives; and
means for analyzing the proposed treatment plan to determine a likelihood that the proposed treatment plan will successfully treat the curernt state, prevent the patient from developing the disease induced by the treatment, and satisfy the treatment objectives.

28. A computer-readable medium containing instructions for controlling a data processing system to perform a method, the data processing system having a healthcare server, the method comprising the steps of:
receiving diagnostic data reflecting a current state of the patient and treatment objectives for the patient;
computing a risk value reflecting a likelihood of the patient developing a disease induced by treatment of the current state based on a subset of the diagnostic data;
receiving a proposed treatment plan for the current state that reflects the computed risk value and the treatment objectives; and 29. The computer-readable medium of claim 28 wherein the analyzing step includes:
receiving patient and provider objectives of treatment indicating a preferred treatment outcome; and
determining whether the treatment plan is consistent with the patient and provider objectives of treatment.

30. The computer-readable medium of claim 28 wherein the step of analyzing includes determining whether the treatment plan is appropriate for the patient's diagnostic data.

31. The computer-readable medium of claim 28 wherein the analyzing step includes determining whether the proposed treatment plan is appropriate based upon prior treatment provided.

32. The computer-readable medium of claim 28 further including instructions for adjusting the compound risk value based on prior outcomes of treatment.

33. The computer-readable medium of claim 28 wherein the receiving step includes accessing diagnostic data stored at a remote location.

34. The computer-readable medium of claim 28 wherein the computing step includes adjusting the risk value based on prior outcomes of treatment.

35. The computer-readable medium of claim 28 further including instructions for transmitting the computed risk value to an external source for pre-authorization of a treatment for the patient.

36. The computer-readable medium of claim 28 wherein the transmitting step includes transmitting the computed risk value to an insurance company.

37. The computer-readable medium of claim 28 wherein the transmitting step includes transmitting the computed risk value to an organization that makes policy decisions pertaining to healthcare benefits.

38. A method in a data processing system, comprising the steps of:
receiving information reflecting a current state of an entity and objectives for the entity;
computing a risk value that indicates a likelihood of the entity entering an undesirable state induced by treatment of the current state based on a subset of the information;
receiving a proposed strategy for the current state that reflects the computed risk value and the objectives; and
analyzing the proposed strategy to determine the likelihood that the proposed strategy will successfully treat the current state, prevent the entity from entering the undesirable state induced by the treatment, and satisfy the objectives.

39. The method of claim 38 further including the step of:
requesting authorization from an external source before employing the proposed strategy.

40. The method of claim 38 further including the step of receiving objectives of the entity and determining whether the proposed strategy is consistent with the objectives of the entity.

41. The method of claim 38 wherein the analyzing step includes determining whether the proposed strategy is appropriate for the diagnostic information.

42. The method of claim 41 wherein the determining step includes determining whether the proposed strategy is appropriate based upon prior results of executed strategies.

43. The method of claim 38 further including the step of adjusting the computed risk value based on prior results of strategy invocations.

44. The method of claim 38 wherein the receiving step includes accessing the diagnostic information from a remote location stored on a remote location.

45. The method of claim 38 wherein the computing step includes adjusting the computed risk value based on prior results of executed strategies.

46. The method of claim 38 wherein the receiving step includes receiving information reflecting a current state of a healthcare patient.

47. A data processing system including a client and healthcare server, comprising:

- means for receiving diagnostic data indicating a current state of a patient;
- means for receiving data reflecting treatment objectives of the patient and the provider indicating a preferred treatment outcome;
- means for receiving a plurality of treatment plans for the current state and for preventing the patient from developing a disease;
- means for computing first risk values for the patient associated with respective ones of the treatment plans, each one of the first risk values being based on a subset of the diagnostic data and indicating a likelihood of the patient developing the disease if the associated treatment plan is followed;
- means for computing second risk values for the patient associated with respective ones of the treatment plans, each one of the second risk values being based on a subset of the diagnostic data and indicating a likelihod of the patient being responsive to treatment of the current state if the associated treatment plan is followed;
- means for receiving an indication of a selected one of the treatment plans;
- means for receiving an indication of a degree of success of the selected treatment plan in treating the current state and preventing the development of the disease;
- means for comparing the degree of success with the treatment objectives to access the effectiveness of the selected treatment plan; and
- means for adjusting the computed first and second risk values for the selected treatment plan based on the effectiveness to increase an accuracy in determining the appropriate treatment.

48. A data processing system including a client and a healthcare server, comprising:

- means for receiving diagnostic data reflecting a current state of the patient;
- means for computing a risk value reflecting a likelihood of the patient being responsive to the treatment of the current state based on a subset of the diagnostic data;
- means for receiving a proposed treatment plan for the current state that reflects the computed risk value; and
- means for analyzing the proposed treatment plan to determine a likelihood that the proposed treatment plan will successfully treat the current state.

* * * * *

UNITED STATES PATENT AND TRADEMARK OFFICE
CERTIFICATE OF CORRECTION

PATENT NO.    : 6,484,144 B2
DATED         : November 19, 2002
INVENTOR(S)   : Dr. John Martin and Randy Nolf It is certified that error appears in the above-identified patent and that said Letters Patent is hereby corrected as shown below:

<u>Title page,</u>
Item [57], ABSTRACT,
Line 3, after "with" insert -- the present invention --.
Line 6, after "embodiment" insert -- of the present invention --.

<u>Column 13,</u>
Table 5, replace "$\geqq$" with -- $\geq$ --.

<u>Column 14,</u>
Table 6B, replace "<" with -- $\leq$ --.

<u>Column 19,</u>
Line 45, after "and" insert a new paragraph.

<u>Column 26,</u>
Line 3, after "; and" insert a new paragraph -- analyzing the proposed treatment plan to determine a likelihood that the proposed treatment plan will successfully treat the current state, prevent the patient from developing the disease induced by the treatment, and satisfy the treatment objectives. --

Signed and Sealed this

Twenty-second Day of July, 2003

JAMES E. ROGAN
*Director of the United States Patent and Trademark Office*